United States Patent
Gibbons et al.

(10) Patent No.: US 12,387,851 B2
(45) Date of Patent: Aug. 12, 2025

(54) EXPOSURE RISK QUANTIFICATION

(71) Applicant: International Business Machines Corporation, Armonk, NY (US)

(72) Inventors: Adam John Gibbons, Oxford (GB); Seumas Mclean Goddard, Lewes (GB); Shivani Joshi, Southampton (GB)

(73) Assignee: International Business Machines Corporation, Armonk, NY (US)

( * ) Notice: Subject to any disclaimer, the term of this patent is extended or adjusted under 35 U.S.C. 154(b) by 264 days.

(21) Appl. No.: 18/350,620

(22) Filed: Jul. 11, 2023

(65) Prior Publication Data

US 2025/0022616 A1   Jan. 16, 2025

(51) Int. Cl.
  *G16H 50/80* (2018.01)
  *H04W 4/02* (2018.01)
  *H04W 4/029* (2018.01)

(52) U.S. Cl.
  CPC ............ *G16H 50/80* (2018.01); *H04W 4/023* (2013.01); *H04W 4/029* (2018.02)

(58) Field of Classification Search
  CPC ....... G16H 50/80; H04W 4/023; H04W 4/029
  USPC ......................... 381/56, 58, 77, 57
  See application file for complete search history.

(56) References Cited

U.S. PATENT DOCUMENTS

| 9,674,625 B2 | 6/2017 | Armstrong-Muntner |
| 2021/0275034 A1* | 9/2021 | Frank ................... A61B 5/6814 |
| 2022/0078575 A1 | 3/2022 | Raveendran et al. |

FOREIGN PATENT DOCUMENTS

| EP | 3716018 A3 | 12/2020 |
| KR | 101471990 B1 | 12/2014 |
| WO | 2022128779 A1 | 6/2022 |

OTHER PUBLICATIONS

Bahle et al., "Using Privacy Respecting Sound Analysis to Improve Bluetooth Based Proximity Detection for COVID-19 Exposure Tracing and Social Distancing", Aug. 20, 2021, Sensors 2021, 21, 5604, pp. 1-26, accessed on Jun. 12, 2023, https://doi.org/10.3390/s21165604.

Hee et al., "Blockchain based Contact Tracing: A Solution using Bluetooth and Sound Waves for Proximity Detection", School of Computing and Data Science, Xiamen University, Malaysia, Sepang, 2022, pp. 1-21, accessed on Jun. 12, 2023, https://eprint.iacr.org/2022/209.

* cited by examiner

*Primary Examiner* — Thjuan K Addy
(74) *Attorney, Agent, or Firm* — Yee & Associates, P.C.

(57) ABSTRACT

The method comprises a first device recording audio data responsive to a wireless proximity contact event with a second device and performing a first Fourier transform on the recorded audio data. The first device sends the first Fourier transform to the second device and receives a second Fourier transform of audio data recorded concurrently by the second device in response to the wireless proximity contact event. The first device, computes a cross correlation of the Fourier transforms and finding a maximum of the cross correlation that constitutes an exposure score. The first device compares the exposure score to a specified threshold that determines whether or not users of the first and second devices have had unacceptable exposure to each other and outputs the exposure score and a binary threshold result.

20 Claims, 6 Drawing Sheets

EXPOSURE RISK QUANTIFICATION

BACKGROUND

The present disclosure relates generally to improve data collection and management, and more specifically to contact tracing utilizing wireless proximity detection.

Contact tracing is a public health practice for identifying individuals who may have come into contact with a source of infectious disease. The goal of contact tracing is to isolate individuals who may be infected to prevent exposure of other individuals. Applications using mobile devices with wireless capabilities such as Bluetooth®, GPS tracking, and similar protocols have been developed to track and notify individuals regarding potential exposure risks.

SUMMARY

An illustrative embodiment provides a method for exposure risk quantification. The method comprises a first device recording audio data responsive to a wireless proximity contact event with a second device and performing a first Fourier transform on the recorded audio data. The first device sends the first Fourier transform to the second device and receives a second Fourier transform of audio data recorded concurrently by the second device in response to the wireless proximity contact event. The first device, computes a cross correlation of the Fourier transforms and finding a maximum of the cross correlation that constitutes an exposure score. The first device compares the exposure score to a specified threshold that determines whether or not users of the first and second devices have had unacceptable exposure to each other and outputs the exposure score and a binary threshold result. According to other illustrative embodiments, a computer system, and a computer program product for exposure risk quantification are provided.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc), or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Figure 1:
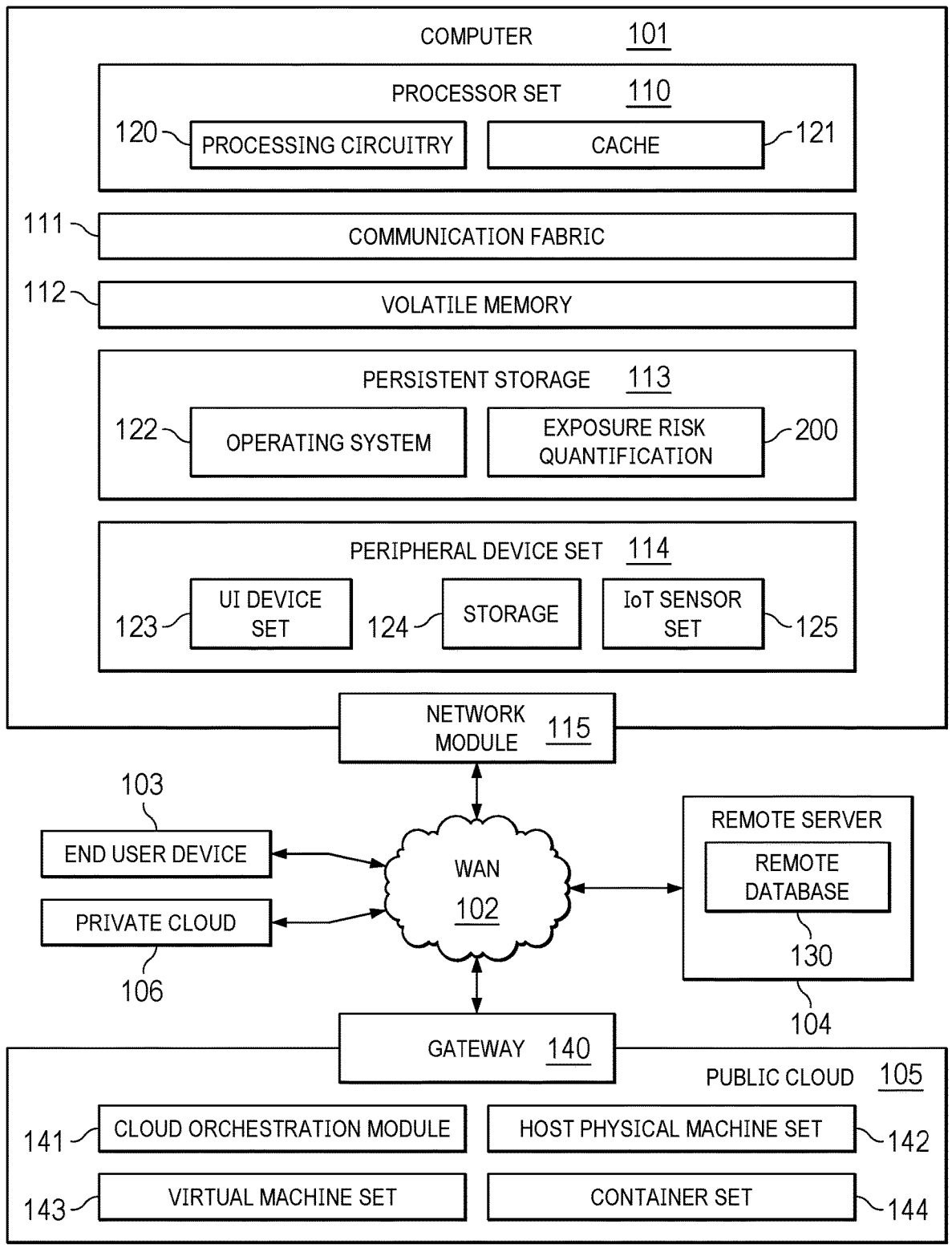
FIG. 1 depicts a pictorial representation of a computing environment in which illustrative embodiments may be implemented.

With reference now to the figures, and in particular, with reference to FIG. 1, a diagram of a data processing environment is provided in which illustrative embodiments may be implemented. It should be appreciated that FIG. 1 is only meant as an example and are not intended to assert or imply any limitation with regard to the environments in which different embodiments may be implemented. Many modifications to the depicted environment may be made.

FIG. 1 depicts a pictorial representation of a computing environment in which illustrative embodiments may be implemented. Computing environment 100 contains an example of an environment for the execution of at least some of the computer code involved in performing the inventive methods, such as exposure risk quantification 200. In addition to exposure risk quantification 200, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and exposure risk quantification 200, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

Computer 101 may take the form of a desktop computer, laptop computer, tablet computer, smart phone, smart watch or other wearable computer, mainframe computer, quantum computer, or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

Processor set 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in exposure risk quantification 200 in persistent storage 113.

Communication fabric 111 is the signal conduction path that allows the various components of computer 101 to communicate with each other. Typically, this fabric is made of switches and electrically conductive paths, such as the switches and electrically conductive paths that make up busses, bridges, physical input/output ports, and the like. Other types of signal communication paths may be used, such as fiber optic communication paths and/or wireless communication paths.

Volatile memory 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

Persistent storage 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data, and re-writing of data. Some familiar forms of persistent storage include magnetic disks and solid state storage devices. Operating system 122 may take several forms, such as various known proprietary operating systems or open source Portable Operating System Interface-type operating systems that employ a kernel. Exposure risk quantification instructions included in block 200 typically includes at least some of the computer code involved in performing the inventive methods.

Peripheral device set 114 includes the set of peripheral devices of computer 101. Data communication connections between the peripheral devices and the other components of computer 101 may be implemented in various ways, such as Bluetooth® connections, Near-Field Communication (NFC) connections, connections made by cables (such as universal serial bus (USB) type cables), insertion-type connections (for example, secure digital (SD) card), connections made through local area communication networks, and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

Network module 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers, and edge servers.

End user device (EUD) 103 is any computer system that is used and controlled by an end user (for example, a customer of an enterprise that operates computer 101) and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

Remote server 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

Public cloud 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economics of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

Private cloud 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

The illustrative embodiments recognize and take into account that Bluetooth® based contact detection is a simple way of determining whether the people carrying those devices have come into contact. In recent years, Bluetooth® has been used for contact tracing during the COVID-19 Pandemic. However, Bluetooth® was designed to connect stably under as many adverse conditions as possible, such as through walls, or at substantial range. As such, transmission of a Bluetooth® signal is generally easier than that of airborne pathogens. This aspect of Bluetooth® recently led to a "pingdemic" wherein large numbers of false positive alerts were sent by contact tracing due to people being in proximity enough for Bluetooth® to flag them, despite substantial other barriers (e.g., walls) in place protecting them from the pathogen. Examples included those living in apartments/flats, where Bluetooth® can pass between all the occupants of the building, but airborne pathogens cannot pass through walls.

The illustrative embodiments also recognize and take into account that slightly more advanced systems use Bluetooth® for ranging as well, which can partially reduce false positives, only flagging positive when people are particularly close, but the issue of not recognising solid barriers remains an issue.

The illustrative embodiments also recognize and take into account that false positives can carry a considerable cost. For example, false positives are estimated to have cost the UK economy £4.6 billion in one month where stringent isolation rules were to be followed after being "pinged." Similar issues can occur worldwide with great impact if implemented the same way and can have far greater impacts if there is no means to advise isolation at all, such as in the absence of automated track and trace services.

The illustrative embodiments provide exposure risk quantification that enhances Bluetooth® based contact detection to overcome the issues noted above and reduce false positives while increasing confidence in contact tracing systems. The illustrative embodiments determine exposure between users of devices by comparing characteristics of audio data recorded concurrently by the devices in response to a wireless proximity triggering event. Devices separated by a substantial physical barrier such as a wall will record audio with significantly different characteristics.

Figure 2:
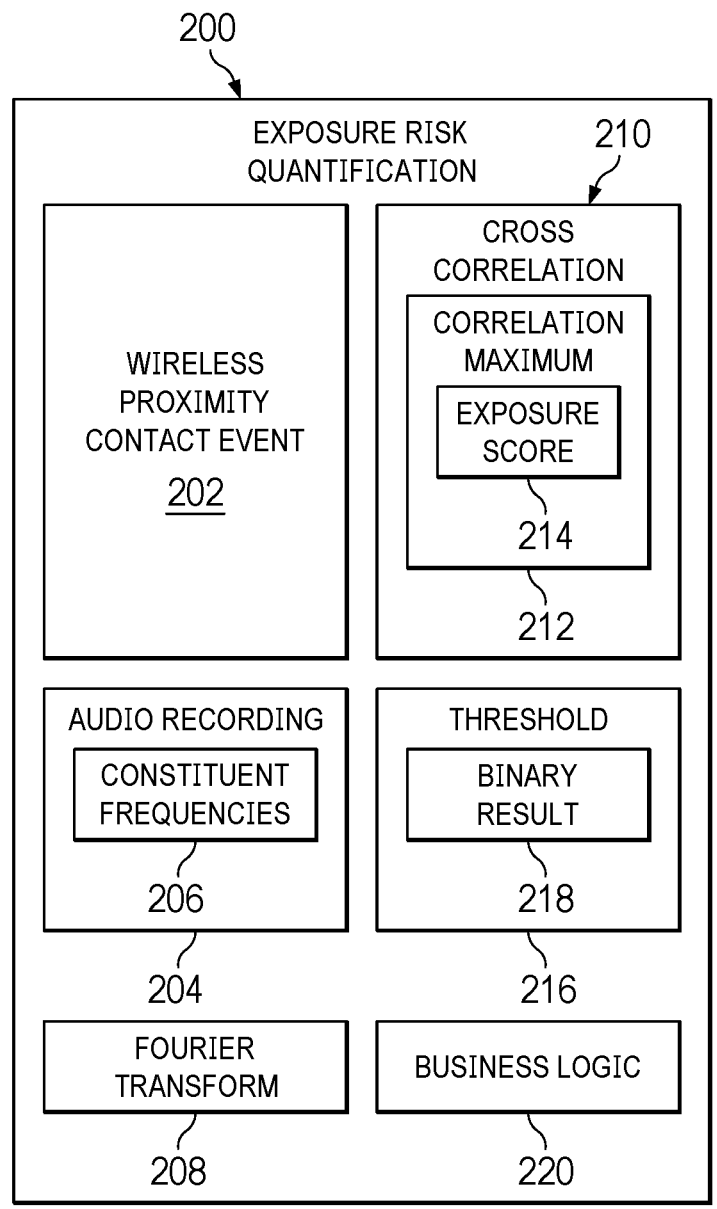
FIG. 2 depicts a block diagram for exposure risk quantification in accordance with an illustrative embodiment.

FIG. 2 depicts a block diagram for exposure risk quantification in accordance with an illustrative embodiment. Exposure risk quantification 200 can be implemented in computing environment 100 in FIG. 1.

Exposure risk quantification 200 is triggered by a wireless proximity contact event 202 between two devices. The wireless contact might be established via Bluetooth®, Near-Field Communications (NFC) or similar short-range wireless communications protocols. The wireless proximity contact event 202 triggers an audio recording 204, which occurs concurrently in the two devices. The audio recording comprises multiple constituent frequencies 206. These constituent frequencies 206 are described by a Fourier transform 208 that is performed by both devices.

The devices exchange Fourier transforms 208 and independently calculate a cross correlation 210 between the transforms. From there, a correlation maximum 212 is found. This correlation maximum constitutes an exposure score 214 between the devices (and their users/bearers).

The exposure score 214 is compared to a threshold 216 to generate a binary result 218. The binary result 218 denotes whether or not the devices have come into unacceptable contact with each other. Based on the exposure score 214 and binary result 218, business logic 220 might be triggered to implements specific notifications and/or policies.

Figure 3:
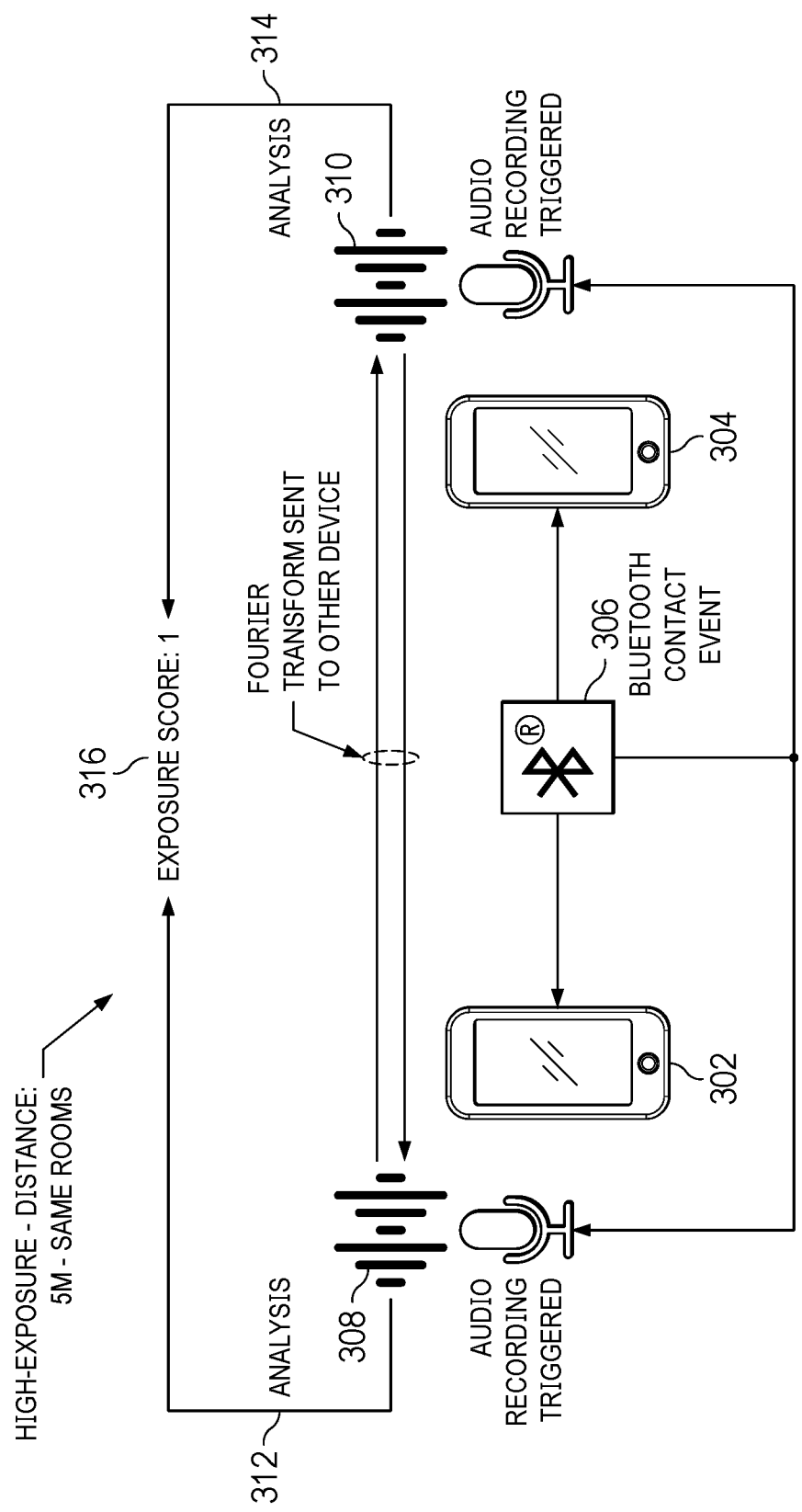
FIG. 3 depicts an example of exposure risk quantification in a situation with high exposure in accordance with an illustrative embodiment.
Figure 4:
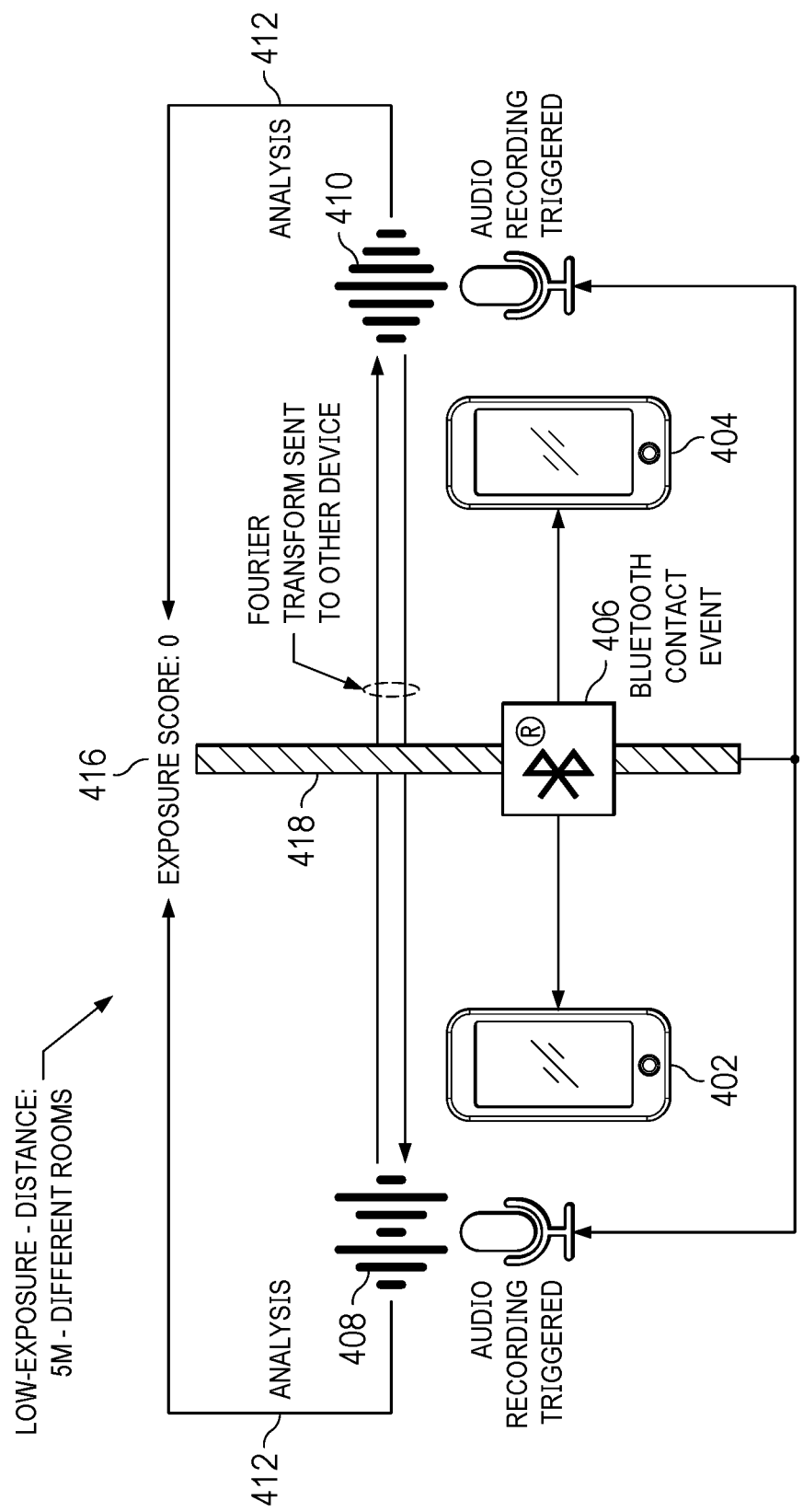
FIG. 4 depicts an example of exposure risk quantification in a situation with low exposure in accordance with an illustrative embodiment.

FIGS. 3 and 4 depict contrasting examples of situations in which devices (and by extension their users) are the same distance from each other but have significantly different exposure risks.

FIG. 3 depicts an example of exposure risk quantification 200 in a situation with high exposure in accordance with an illustrative embodiment. In this example, mobile phones 302, 304 are located five meters apart in the same room.

When the mobile phones 302, 304 come within specific proximity range they trigger a Bluetooth® contact event 306. This Bluetooth® contact event 306 triggers respective audio recordings 308, 310 by both mobile phones 302, 304.

The mobile phones 302, 304 exchange Fourier transforms of their respective audio recordings 308, 310 such that each device is able to analyze both Fourier transforms. The mobile phones 302, 304 perform independent analyses 312, 314 (see FIG. 5) based on the Fourier transforms to arrive at an exposure score 316. The exposure score 320 can be expressed as a value between 0 and 1. In the present example, the similarities in acoustic characteristics of the two audio recordings 308, 310 produce an exposure score of 1, indicating that the mobile phones 302, 304 (and their respective users) are in the same room and in close enough proximity to constitute high exposure.

FIG. 4 depicts an example of exposure risk quantification 200 in a situation with low exposure in accordance with an illustrative embodiment. In this example, mobile phones 402, 404 are located five meters apart but in separate rooms.

The principles of operation are the same as in FIG. 3. A Bluetooth® contact event 406 triggers respective audio recordings 408, 410 by both mobile phones 402, 404. Though mobile phones 402 and 404 are separated by the same distance as phones 302 and 304 in FIG. 3, being in separate rooms on either side of wall 418 results in significant differences in audio recordings 408, 410. These differences are the result of different environmental factors in the rooms such as, e.g., background noises, furniture, etc., that make the respective acoustic characteristics of each room different from the other.

As in FIG. 3, the mobile phones 402, 404 exchange Fourier transforms of their respective audio recordings 408, 410 and perform their own independent analyses 412, 414 to arrive at an exposure score 416. In the present example, the differences in acoustic characteristics of the two audio recordings 408, 410 produce an exposure score of 0, indicating that the mobile phones 402, 404 (and their respective users) are in different rooms and therefore have low exposure to each other.

Figure 5:
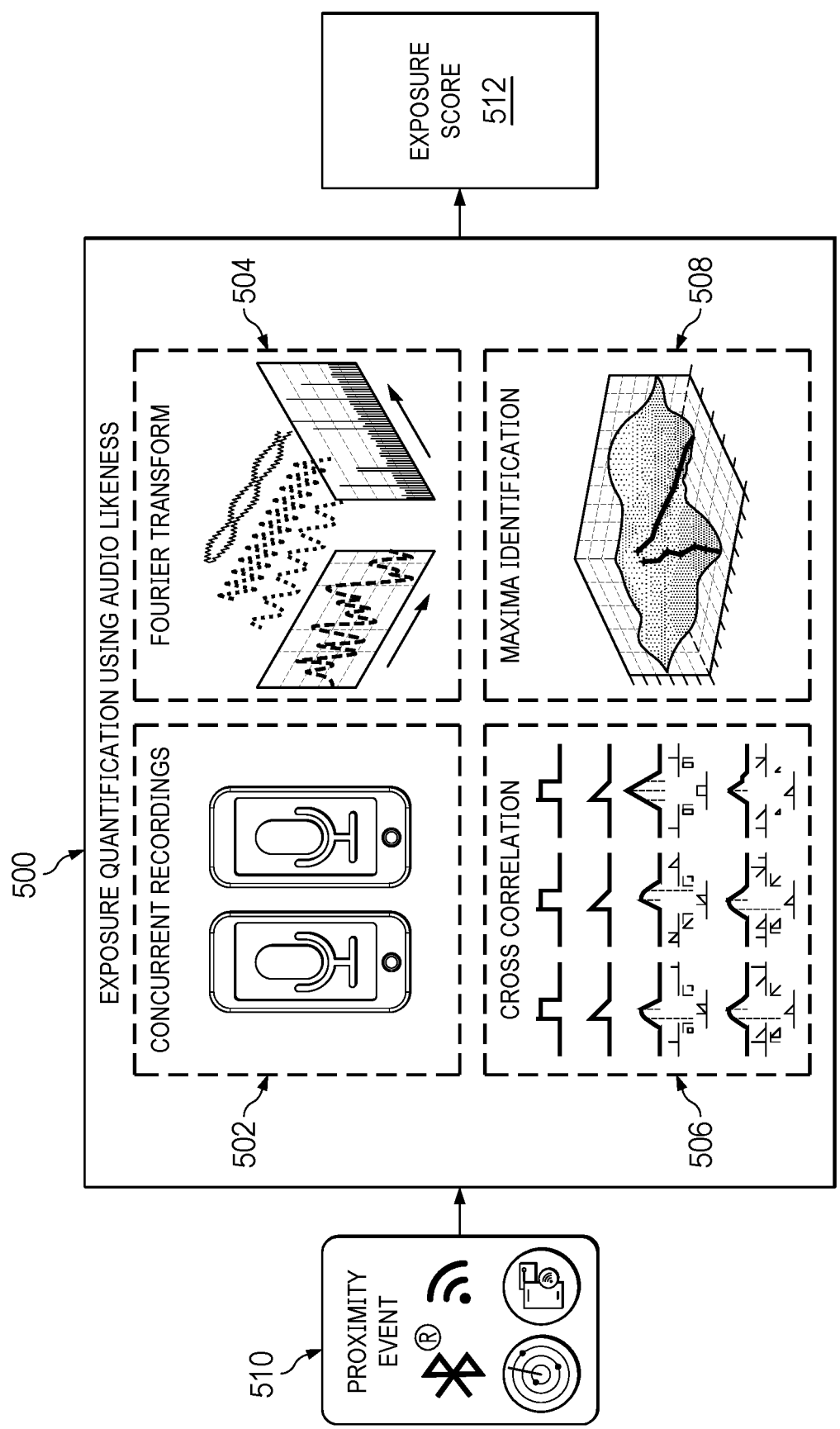
FIG. 5 depicts an exposure quantification using audio likeness (EQUAL) analysis model in accordance with an illustrative embodiment.

FIG. 5 depicts an exposure quantification using audio likeness (EQUAL) analysis model in accordance with an illustrative embodiment. EQUAL model 500 represented the analytical framework used by the devices participating the exposure quantification. A Bluetooth® contact event 510 triggers concurrent audio recordings 502 on both devices. The devices take these concurrent audio recordings 502 and calculate the corresponding Fourier transforms 504 to extract the time series frequency content of the audio data. A Fourier transform decomposes a signal into its constituent frequencies by taking a time-domain representation of the signal and converting it into a frequency-domain representation. Each device performs a Fourier transform on its audio recording and sends it to the other device. For security applications, the Fourier transforms 504 can be obfuscated and/or one way. After the Fourier transform, the original audio recordings 502 can be deleted to comply with security and/or privacy policies.

Using both Fourier transforms 504, each device can independently computer a cross correlation 506 of the Fourier data. After computation of the cross correlation 506, the Fourier transforms 504 may also be deleted.

The cross correlation 506 provides a similarity score over varying time offsets of the two audio recordings 502. From there, the devices identify maximum 508 of the cross correlation using methods such as gradient ascent, simulated annealing, etc. This maximum becomes the exposure score 512 (between 0 and 1).

EQUAL model 500 creates a score 512 that inversely correlates the extent of audio attenuation and disruption between two devices. This score can be combined with the Bluetooth® proximity score to identify not only proximity but also the likelihood of sharing the same air. For example, the carriage of sound waves can act as an analogue to the carriage of pathogens.

The exposure score 512 can be thresholded to determine whether or not the users of the devices have come into unacceptable contact with each other. The resulting output is a tuple comprising the exposure score 512 (between 0 and 1) and a binary threshold result. Business logic such as track and trace services can be triggered based upon the outcome of the thresholding and/or exposure score.

The model and processing steps of the illustrative embodiments can be generalized and applied to a variety of proximity, locating, or security contexts. For example, the illustrative embodiments can be deployed as a countermeasure to provide eavesdropping warnings, provide accurate and/or less expensive room occupancy monitoring, as well as other applications that benefit from identifying physical barriers in addition to basic radio frequency (RF) detection. The illustrative embodiments can improve the sensitivity and accuracy of safety and security systems both within and outside the workplace, producing more concise and meaningful notifications.

Figure 6:
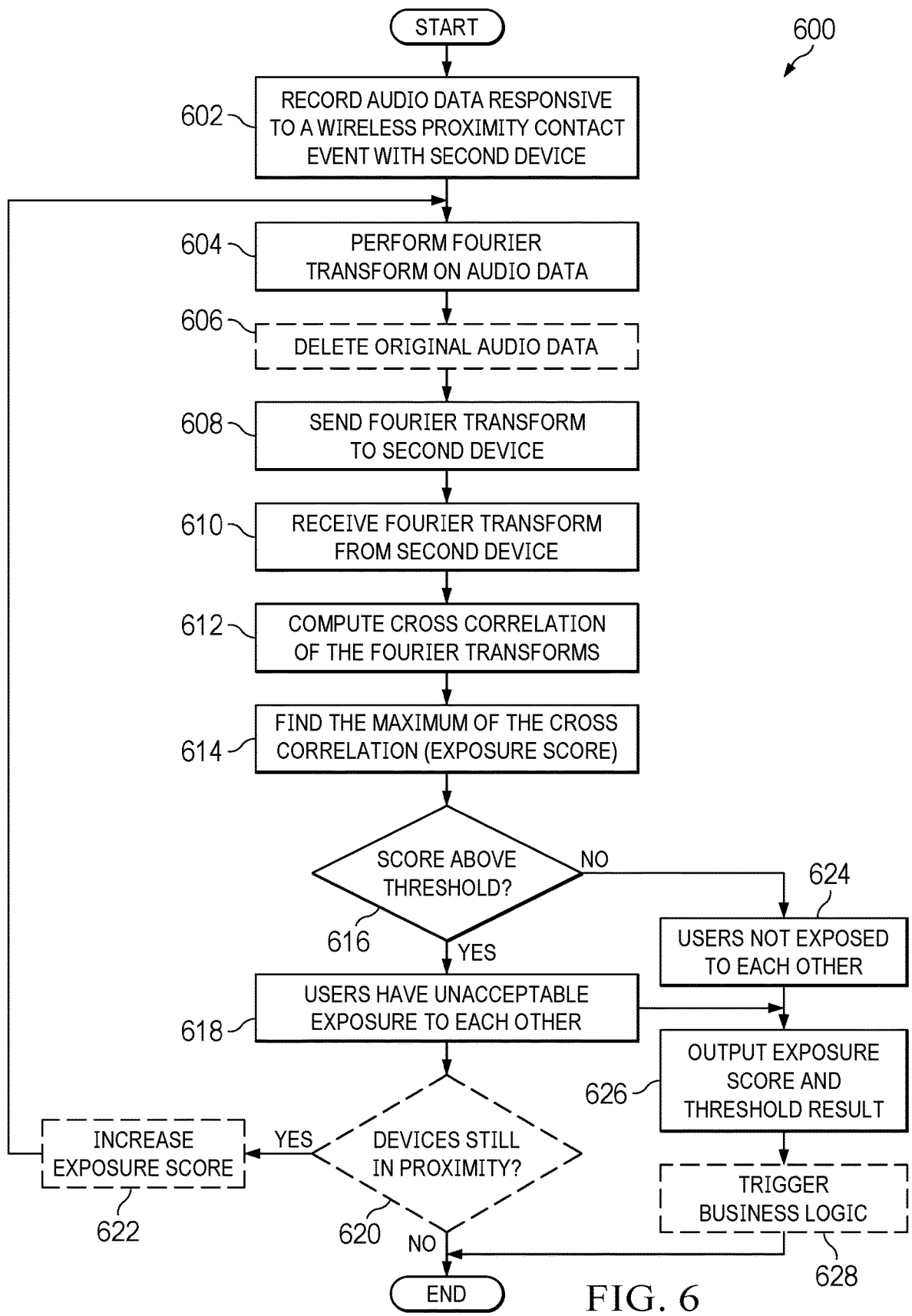
FIG. 6 depicts a flowchart for exposure risk quantification in accordance with an illustrative embodiment.

FIG. 6 depicts a flowchart for exposure risk quantification in accordance with an illustrative embodiment. Process 600 can be carried out in computing environment 100 in FIG. 1.

Process 600 begins by a first device recording audio data responsive to a wireless proximity contact event with a second device (step 602). Examples of such devices include mobile devices, mobile phones, smart watches, laptop computers, tablet computers, desktop computers, and fixed base stations.

The first device performs a first Fourier transform on the recorded audio data (step 604). In performing the Fourier transform, the first device might divide the audio data into lower resolution time intervals, wherein each time interval is integrated over time such that the Fourier transform is irreversible. For example, the Fourier transform might be averaged over intervals of one second rather than instantaneously. Optionally, the first device might delete the recorded audio data after performing the first Fourier transforms (step 606).

The first device sends the first Fourier transform to the second device (step 608) and receives a second Fourier transform from the second device of audio data recorded by the second device concurrently with the first device in response to the wireless proximity contact event (step 610). Either or both devices might remove a subset of frequency bands from the respective Fourier transforms before sending the Fourier transforms to each other.

The first device computes a cross correlation of the Fourier transforms (step 612) and finds a maximum of the cross correlation, wherein the maximum constitutes an exposure score (step 614).

The first device compares the exposure score to a specified threshold that determines whether or not users of the first and second devices have had unacceptable exposure to each other (step 616). If the exposure score is below the threshold (e.g., because there is a wall separating the devices) the users are deemed not to be unacceptably exposed to each other (step 624). If the exposure score exceeds the threshold the users of the first and second devices are deemed to have unacceptable exposure to each other (step 618).

Optionally, responsive to a determination that the users of the first and second devices have had unacceptable exposure to each other and that the devices are still in wireless proximity contact (step 620), the first device might repeat the steps 604 through 614 at specified time intervals (e.g., every 10 seconds) as long as the first device and second device remain in wireless proximity contact, wherein a previous exposure score is added to a subsequent exposure score with each iteration (step 622).

The first device output the exposure score and a binary threshold result (step 626). Optionally, the output might trigger business logic based on at least one of the exposure score or threshold result (step 628). For example, the business logic might report to a track and tracing service that can be referenced at a later time, e.g., to help distribute medication in cases of pathogen exposure. As another example, the business logic might trigger a notification on a device, whether the same device involved in recording and comparing audio or another device used by the other. Process 600 then ends.

As used herein, a "number of," when used with reference to objects, means one or more objects. For example, a "number of different types of networks" is one or more different types of networks.

Further, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

As used herein, a "computer instruction," or "computer program", means one step or a set of steps that includes information on how to operate, perform, or maintain particular computer software or hardware. For example, a "computer instruction" can be a computer program instruction in the form of lines of code or source code that are executable by a computer system.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component can be configured to perform the action or operation described. For example, the component can have a configuration or design for a structure that provides the component an ability to perform the action or operation that is described in the illustrative examples as being performed by the component. Further, to the extent that terms "includes", "including", "has", "contains", and variants thereof are used herein, such terms are intended to be inclusive in a manner similar to the term "comprises" as an open transition word without precluding any additional or other elements.

The descriptions of the various embodiments of the present disclosure have been presented for purposes of illustration but are not intended to be exhaustive or limited to the embodiments disclosed. Not all embodiments will include all of the features described in the illustrative examples. Further, different illustrative embodiments may provide different features as compared to other illustrative embodiments. Many modifications and variations will be apparent to those of ordinary skill in the art without departing from the scope and spirit of the described embodiment. The terminology used herein was chosen to best explain the principles of the embodiment, the practical application or technical improvement over technologies found in the marketplace, or to enable others of ordinary skill in the art to understand the embodiments disclosed here.

What is claimed is:

1. A method of exposure risk quantification, the method comprising:
   recording, by a first device, audio data responsive to a wireless proximity contact event with a second device;
   performing, by the first device, a first Fourier transform on the recorded audio data;
   sending, by the first device, the first Fourier transform to the second device;
   receiving, by the first device, a second Fourier transform from the second device, wherein the second Fourier transform is of audio data recorded by the second device concurrently with the first device in response to the wireless proximity contact event;
   computing, by the first device, a cross correlation of the Fourier transforms;
   finding, by the first device, a maximum of the cross correlation, wherein the maximum constitutes an exposure score;
   comparing, by the first device, the exposure score to a specified threshold that determines whether or not users of the first and second devices have had unacceptable exposure to each other; and
   outputting, by the first device, the exposure score and a binary threshold result.

2. The method of claim 1, further comprising deleting the recorded audio data after performing the Fourier transform.

3. The method of claim 1, further comprising removing, by the first device, a subset of frequency bands from the first Fourier transform before sending the first Fourier transform to the second device.

4. The method of claim 1, further comprising dividing, by the first device, the audio data into lower resolution time intervals, wherein each time interval is integrated over time such that the first Fourier transform is irreversible.

5. The method of claim 1, wherein the first device comprises at least one of:
   mobile devices;
   mobile phones;
   smart watches;
   laptop computers;
   tablet computers;
   desktop computers; or
   fixed base stations.

6. The method of claim 1, further comprising, responsive to a determination that users of the first and second devices have had unacceptable exposure to each other, recalculating, by the first device, the exposure score at specified time intervals as long as the first device and second device remain in wireless proximity contact, wherein a previous exposure score is added to a subsequent exposure score with each iteration.

7. The method of claim 1, further comprising triggering business logic based on at least one of the exposure score or threshold result.

8. A system for exposure risk quantification, the system comprising:
   a first device with persistent storage to store program instructions;
   one or more respective processors on the first device, wherein the processors are operably connected to the respective persistent storage and configured to execute the program instructions to cause the first device to:
   record audio data responsive to a wireless proximity contact event with a second device;
   perform a first Fourier transform on the recorded audio data;
   send the first Fourier transform to the second device;
   receive a second Fourier transform from the second device, wherein the second Fourier transform is of audio data recorded by the second device concurrently with the first device in response to the wireless proximity contact event;
   compute a cross correlation of the Fourier transforms;
   find a maximum of the cross correlation, wherein the maximum constitutes an exposure score;
   compare the exposure score to a specified threshold that determines whether or not users of the first and second devices have had unacceptable exposure to each other; and
   output the exposure score and a binary threshold result.

9. The system of claim 8, wherein the program instructions further cause the first device to delete the recorded audio data after performing the first Fourier transform.

10. The system of claim 8, wherein the program instructions further cause the first device to remove a subset of frequency bands from the first Fourier transform before sending the first Fourier transform to the second device.

11. The system of claim 8, wherein the program instructions further cause the first device to divide the audio data into lower resolution time intervals, wherein each time interval is integrated over time such that the Fourier transform is irreversible.

12. The system of claim 8, wherein the first devices comprises at least one of:
    mobile devices;
    mobile phones;
    smart watches;
    laptop computers;
    tablet computers;
    desktop computers; or
    fixed base stations.

13. The system of claim 8, wherein the program instructions further cause the first device, responsive to a determination that users of the first and second devices have had unacceptable exposure to each other, to recalculate the exposure score at specified time intervals as long as the first device and second device remain in wireless proximity contact, wherein a previous exposure score is added to a subsequent exposure score with each iteration.

14. The system of claim 8, wherein the program instructions further cause the first device to trigger business logic based on at least one of the exposure score or threshold result.

15. A computer program product for exposure risk quantification, the computer program product comprising:
    persistent storage media on a first device, wherein the persistent storage media has program instructions configured to cause one or more processors on the first device to:
    record audio data responsive to a wireless proximity contact event with a second device;
    perform a first Fourier transform on the recorded audio data;
    send the first Fourier transform to the second device;
    receive a second Fourier transform from the second device, wherein the second Fourier transform is of audio data recorded by the second device concurrently with the first device in response to the wireless proximity contact event;

compute a cross correlation of the Fourier transforms;

find a maximum of the cross correlation, wherein the maximum constitutes an exposure score;

compare the exposure score to a specified threshold that determines whether or not users of the first and second devices have had unacceptable exposure to each other; and output the exposure score and a binary threshold result.

16. The computer program product of claim 15, wherein the program instructions further cause the processors to delete the recorded audio data after performing the first Fourier transform.

17. The computer program product of claim 15, wherein the program instructions further cause the processors to remove a subset of frequency bands from the first Fourier transform before sending the first Fourier transforms to the second device.

18. The computer program product of claim 15, wherein the program instructions further cause the processors to divide the audio data into lower resolution time intervals, wherein each time interval is integrated over time such that the first Fourier transform is irreversible.

19. The computer program product of claim 15, wherein the program instructions further cause the processors to, responsive to a determination that users of the first and second devices have had unacceptable exposure to each other, recalculate the exposure score at specified time intervals as long as the first device and second device remain in wireless proximity contact, wherein a previous exposure score is added to a subsequent exposure score with each iteration.

20. The computer program product of claim 15, wherein the program instructions further cause the processors to trigger business logic based on at least one of the exposure score or threshold result.

* * * * *